(12) United States Patent
Liang et al.

(10) Patent No.: US 9,938,586 B2
(45) Date of Patent: *Apr. 10, 2018

(54) **METHODS FOR GENETIC ANALYSIS OF TEXTILES MADE OF *GOSSYPIUM BARBADENSE* AND *GOSSYPIUM HIRSUTUM* COTTON**

(71) Applicants: MingHwa Benjamin Liang, East Setauket, NY (US); Stephane Shu Kin So, Stony Brook, NY (US)

(72) Inventors: MingHwa Benjamin Liang, East Setauket, NY (US); Stephane Shu Kin So, Stony Brook, NY (US)

(73) Assignee: APDN (B.V.I.) INC., Tortola (VG)

( * ) Notice: Subject to any disclaimer, the term of this patent is extended or adjusted under 35 U.S.C. 154(b) by 650 days.

This patent is subject to a terminal disclaimer.

(21) Appl. No.: 14/191,947

(22) Filed: Feb. 27, 2014

(65) Prior Publication Data

US 2014/0295423 A1  Oct. 2, 2014

Related U.S. Application Data

(63) Continuation of application No. 12/269,737, filed on Nov. 12, 2008, now Pat. No. 8,669,079.

(51) Int. Cl.
*C12Q 1/68* (2018.01)
*C12P 19/34* (2006.01)

(52) U.S. Cl.
CPC ..... *C12Q 1/6895* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 8,940,485 | B2 * | 1/2015 | Liang | C12Q 1/6895 435/6.11 |
| 9,290,819 | B2 * | 3/2016 | Liang | C12Q 1/6895 |
| 2011/0289022 | A1 * | 11/2011 | Arioli | C12Q 1/6881 705/500 |

OTHER PUBLICATIONS

Cronn et al. (2002) American Journal of Botany vol. 89(4): pp. 707-725.
Dolnik et al. (2000) Electrophoresis vol. 21 : pp. 41-54.
Yang et al. (2005) Plant cell Rep vol. 24:237-245.
Han et al. (published on line Dec. 9, 2005) Theoretical and Applied Genetics (2006) 112:430-439.

* cited by examiner

*Primary Examiner* — Young J Kim
(74) *Attorney, Agent, or Firm* — Hoffmann & Baron, LLP

(57) ABSTRACT

Methods for distinguishing between cotton species by analyzing a sample of mature cotton fibers from raw cotton materials or from textile goods are disclosed. DNA is extracted from the mature cotton fiber sample and subjected to PCR techniques which enable the identification of the species of cotton utilized in the textile or cotton material of interest.

22 Claims, 5 Drawing Sheets

METHODS FOR GENETIC ANALYSIS OF TEXTILES MADE OF *GOSSYPIUM BARBADENSE* AND *GOSSYPIUM HIRSUTUM* COTTON

RELATED APPLICATIONS

This application is a continuation of U.S. patent application Ser. No. 12/269,737 filed Nov. 12, 2008 and simultaneously co-filed with the patent application Ser. No. 12/269,757 titled "Methods for Genotyping Mature Cotton Fibers and Textiles." Each of the parent application and referenced co-filed patent application are hereby incorporated by reference herein in their entireties.

FIELD

This invention pertains to methods for analyzing mature cotton fibers for the detection of genetic variations among a variety of cotton species, particularly, the genetic variations between cotton species *Gossypium barbadense* and *Gossypium hirsutum*.

BACKGROUND

In general, there are two major types of cotton species being cultivated throughout the world, namely *Gossypium barbadense* and *Gossypium hirsutum*. These two species are from the genus *Gossypium*, which comprises at least 40 different cotton species. *Gossypium barbadense* (sea island cotton) and *Gossypium hirsutum* (upland cotton) are allotetraploids and are known as New World cotton or "American" cotton. There are striking differences in the physical characteristics of the cotton fibers produced by *G. barbadense* compared to the cotton fibers produced by *G. hirsutum*. *G. barbadense* produces longer cotton fibers than most other cotton species and these fibers are usually called "extra long staple" (ELS) fibers, while those of *G. hirsutum* are shorter and are called or defined as "upland" fibers. Textiles made of ELS fibers are considered to be of higher quality compared to textiles made with shorter fibers, like those produced by *G. hirsutum* cotton plants. Thus, textiles produced from ELS cotton fibers are considered more valuable in the textile marketplace.

There have been many studies trying to manipulate cotton genes for fiber quality improvement (U.S. Pat. Nos. 6,169,174; 7,060,874; and 6,995,256), enhanced pesticide toxin production (U.S. Pat. Nos. 6,686,149; 6,140,075; and 6,057,370), and herbicide resistance (U.S. Pat. No. 7,223,906). There have also been studies investigating the genetic polymorphism of various cotton species using PCR-based markers (J. Applied Sci. Res. 3(10)1156-1169, 2007). However, no success has been found in the categorization of cotton cultivars using genetic markers on mature cotton fibers mainly because of the lack of efficient primers to amplify fragmented DNA in mature cotton fibers.

Unfortunately, once cotton fibers are processed and made into yarn and/or fabrics most physical properties have been altered, and there is no reliable method to determine the origin or species of the fibers utilized to produce the yarn or textile(s). Forging clothing or producing knock-off textile items is a serious problem for the textile industry, costing manufacturers and retail stores millions and perhaps billions of dollars annually, in the United States alone. Being able to identify the species of cotton utilized in a textile item would not only be a way to authenticate an item as legitimate, but would also enable the detection of forged or counterfeit textile products.

SUMMARY

Methods for authenticating articles of manufacture containing cotton fibers such as garments or other textile goods are described. Higher quality cotton textile goods are typically made from *Gossypium barbadense* known to have Extra Long Staple (ELS) cotton fibers. Counterfeit textile goods are often made with different, inferior cotton with shorter fibers, such as *Gossypium hirsutum*. When the cotton species in an original textile article is known, the detection of a different species of cotton in the textile articles subsequent to manufacture will indicate that a counterfeit article has been substituted. The methods provide a means for identifying the cotton species in a textile item from a sample of mature cotton fibers taken from the textile item, and for authenticating the textile items based on the identification of the cotton species. The authentication can be carried out at different points along the supply or commerce chain between manufacture and retail sale to identify the point in the chain at which counterfeit goods are introduced.

In one embodiment, the method for identifying cotton species comprises collecting cotton fibers from a sample, extracting genomic DNA from the collected cotton fibers, and amplifying the DNA with PCR-based techniques, followed by analyzing the amplified product to distinguish between a first cotton species and a second cotton species. In the illustrative embodiment the first cotton species is *G. barbadense* and the second cotton species is *G. hirsutum*. In other embodiments, the first cotton species is selected from the group consisting of *G. barbadense, G. hirsutum, G. arboreum* or *G. herbaceum*. In still other embodiments, the second cotton species is selected from the group consisting of *G. barbadense, G. hirsutum, G. arboreum* or *G. herbaceum*.

Further, in some embodiments the sample is a textile item while in other embodiments the sample is raw cotton material.

In certain embodiments, the amplifying further comprises using at least one set of specific primers which targets sequence polymorphism between the first cotton species and the second cotton species.

In some embodiments, the genomic DNA extracted from the cotton fibers originating from the textile in question comprises chloroplast DNA and in other embodiments it comprises nuclear DNA.

In certain embodiments, the targeted sequences of the first cotton species and the second cotton species have different detectable physical characteristics.

In some embodiments, the detectable physical characteristic of the targeted sequence is a difference in sequence length for the first cotton species compared to the second cotton species.

In other embodiments, the detectable physical characteristic of the targeted sequence is a different sequence composition for the first and second cotton species.

In most embodiments the analyzing of the amplified products comprises detecting the size of the amplified products by capillary electrophoresis. In other embodiments gel electrophoresis may be utilized instead of capillary electrophoresis.

One embodiment of the method for verifying a textile article comprises collecting cotton fibers from a textile item, extracting genomic DNA from the cotton fibers collected, amplifying said DNA with PCR-based techniques, analyzing the amplified product to distinguish between a first cotton species and a second cotton species, identifying the cotton fibers from the textile item as belonging to the first cotton species or to the second cotton species, and determining from the identified cotton species if the textile article is authentic. In most embodiments for verifying a textile article, the first cotton species is *G. barbadense* and the second cotton species is *G. hirsutum*. In some embodiments for verifying a textile article, the amplifying further comprises using at least one set of specific primers which target sequence polymorphism between the first cotton species and the second cotton species. Also, the targeted sequences of the first cotton species and the second cotton species have different detectable physical characteristics. The detectable physical characteristic can be a difference in length of the targeted sequence when comparing the first and second cotton species to one another. The detectable physical characteristic can also be a slight variation in sequence composition.

In one embodiment of a kit useful for carrying out the methods of the invention, the kit comprises a sample collection tube for placing mature cotton fibers obtained from the textile item, a DNA extraction solution, at least one set of specific primers specific for a target sequence found in a first cotton species and a second cotton species, as well as a PCR amplification buffer solution.

In some embodiments the kit for determining the cotton species of a sample or item further comprises a PCR instrument.

In yet other embodiments, the kit may further be found comprising an internal control for comparing the size of the amplified product.

In certain embodiments, the kit comprises a capillary electrophoresis device.

All patents and publications identified herein are incorporated herein by reference in their entirety.

DESCRIPTION

Definitions

Figure 1:
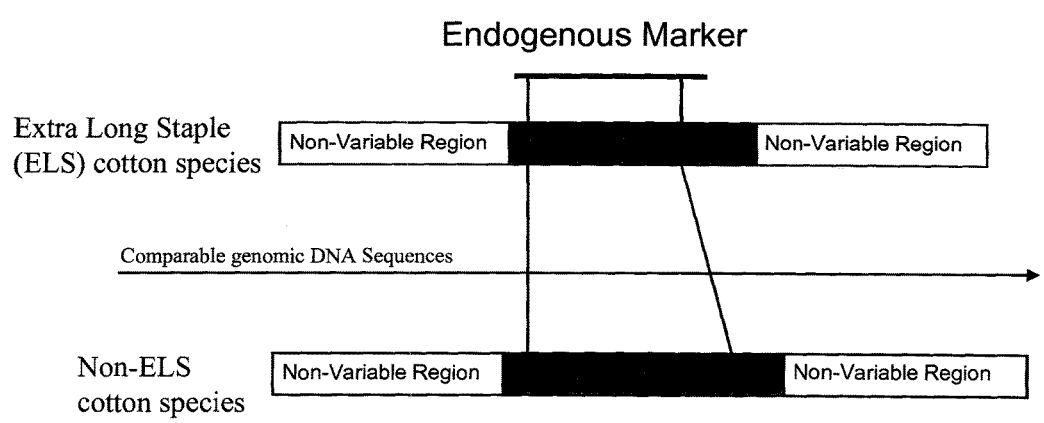
FIG. 1 is a diagram showing the comparison of a genetic variable region of two different cotton.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Optional" or "optionally" means that the subsequently described event or circumstance may occur but need not occur, and that the description includes instances where the event or circumstance occurs and instances in which it does not.

The terms "those defined above" and "those defined herein" when referring to a variable incorporates by reference the broad definition of the variable as well as preferred, more preferred and most preferred definitions, if any.

The term "ELS" means "extra long staple" cotton fibers. For example, those fibers produced from *G. barbadense* are ELS cotton fibers.

The term "Upland fiber" defines cotton fibers which are shorter than ELS cotton fibers. For example, upland fibers are produced from *G. hirsutum*.

The term "genomic DNA" means the full complement of DNA contained in the genome of a cell or organism. This includes nuclear DNA as well as DNA stored within organelles, such as the mitochondrial genome (mDNA) and the chloroplast genome (cpDNA).

The term "variable region" means a genetic region of similar cotton species which has sequence variation between comparing species. The variation may be for example, a difference in sequence length within a genetic region, or single nucleotide changes within a specific genetic region.

The term "primer" means an oligonucleotide with a specific nucleotide sequence which is sufficiently complimentary to a particular sequence of a target DNA molecule, such that the primer specifically hybridizes to the target DNA sequence.

The term "probe" refers to a binding component which binds preferentially to one or more targets (e.g., antigenic epitopes, polynucleotide sequences, macromolecular receptors) with an affinity sufficient to permit discrimination of labeled probe bound to target from nonspecifically bound labeled probe (i.e., background).

The term "probe polynucleotide" means a polynucleotide that specifically hybridizes to a predetermined target polynucleotide.

The term "oligomer" refers to a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure.

The term "PCR" refers to polymerase chain reaction. This refers to any technology where a nucleotide sequence is amplified via temperature cycling techniques in the presence of a nucleotide polymerase, preferably a DNA polymerase. This includes but is not limited to real-time PCR technology, reverse transcriptase-PCR, and standard PCR methods.

The term "nucleic acid" means a polymer composed of nucleotides, e.g. deoxyribonucleotides or ribonucleotides, or compounds produced synthetically which can hybridize with naturally occurring nucleic acids in a sequence specific manner analogous to that of two naturally occurring nucleic acids, i.e., can participate in hybridization reactions, e.g., cooperative interactions through Pi electron stacking and hydrogen bonds, such as Watson-Crick base pairing interactions, Wobble interactions, etc.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "polynucleotide" refers to a single or double stranded polymer composed of nucleotide monomers of generally greater than 50 nucleotides in length.

The term "monomer" as used herein refers to a chemical entity that can be covalently linked to one or more other such entities to form an oligomer. Examples of "monomers" include nucleotides, amino acids, saccharides, peptides, and the like.

The term "identifiable sequence" or "detectable sequence" means a nucleotide sequence which can by detected by hybridization and/or PCR technology by a primer or probe designed for specific interaction with the target nucleotide sequence to be identified. The interaction of the target nucleotide sequence with the specific probe or primer can be detected by optical and/or visual means to determine the presence of the target nucleotide sequence.

In general, the term "textile" may be used to refer to fibers, yarns, or fabrics. More particularly, the term "textile" as used herein refers to raw cotton, ginned cotton, cotton fibers, cotton yarns, cotton fabrics, yarn that is blended with cotton, fabric that is blended with cotton, or any combination thereof.

The term "mature cotton fiber" as used herein refers to a cotton fiber having a lumen wall that separates the secondary wall (consisting of cellulose) from the lumen that has naturally collapsed. The lumen is the hollow canal that runs the length of the fiber and is filled with living protoplast during the growth period; after the fiber matures and the boll opens the protoplast dries up and the lumen will naturally collapse and leave a large central void in each fiber.

The present specification describes methods for identifying and verifying the cotton species of mature cotton fibers. The methods enable cotton species identification of raw cotton bales for import/export purposes, identification of the origin of a particular cotton in raw or manufactured form, as well as identifying the cotton species in yarn and manufactured garments. In particular, the invention relates to verifying the type/species of cotton used in the manufacturing of an article comprising cotton. Most of the cotton textiles produced are made from two different cotton species, *G. barbadense* and *G. hirsutum*.

The methods allow a user to genetically identify textiles made of *G. barbadense* and *G. hirsutum* cotton fibers. The process involves extracting DNA from mature cotton fibers or textiles and amplifying DNA using specific primers and the Polymerase Chain Reaction (PCR) method. Specific primers targeting regions exhibiting sequence variation or sequence polymorphism between *G. barbadense* and *G. hirsutum* were used to distinguish between species.

There are subtle genetic variations in the genetic makeup of the two cotton species. The methods provide genetic tests which definitively identify fibers and textiles as being made of either *G. barbadense* or *G. hirsutum* cotton. The methods utilize at least one variable sequence region found within the cotton genomes of interest, which allows the cotton species to be distinguished from one another. In general, to identify cotton fibers originated from either *G. barbadense* or *G. hirsutum*, endogenous genetic markers based on the genetic variation between these two species were utilized, as depicted in FIG. 1.

FIG. 1 is a diagram showing the comparison of a genetic variable region of an Extra Long Staple (ELS) cotton species (e.g. *G. barbadense*) to a Non-ELS cotton species (e.g. *G. hirsutum*). A variable region can differ in either DNA length or DNA sequence, while the non-variable regions have identical DNA sequences between the species being compared. Thus, the variable region can be utilized as an endogenous marker to distinguish between cotton species. By targeting regions of the DNA genome(s), which have sequence variations such as the region depicted in FIG. 1, the mature cotton fibers can be identified as either *G. barbadense* or *G. hirsutum* by the length or size of the target sequence. The method allows for cotton sequence-specific simple sequence repeats (SSRs) associated primers to be used for cotton species differentiation. This allows for the use of SSRs primers to detect endogenous markers with varying DNA length polymorphisms between the different species.

In other embodiments, the methods utilize SNP or haplotyping to distinguish different cotton species. Primers are designed to amplify DNA fragments containing SNP/haplotypes and then the amplified DNA fragments are analyzed by sequencing. SNP analysis kits are available, such as the TaqMan™ kit by ABI, or SNP analysis can be carried out by a synthesis method, such as Pyrosequencing™.

While sequence length is the physical characteristic targeted by the endogenous marker shown in FIG. 1, the physical characteristic used to identify the cotton fibers as *G. barbadense* or *G. hirsutum* could be differences in site specific mutations which can be detected by specific nucleotide probes designed for a specific portion of the target sequence of each cotton species of interest. By utilizing a partial difference in sequence composition between the cotton species of interest, probes can be designed to detect one cotton species and not the other. The probes can be arranged in a high throughput array setup, to analyze and authenticate a large number of samples at one time.

Figure 2:
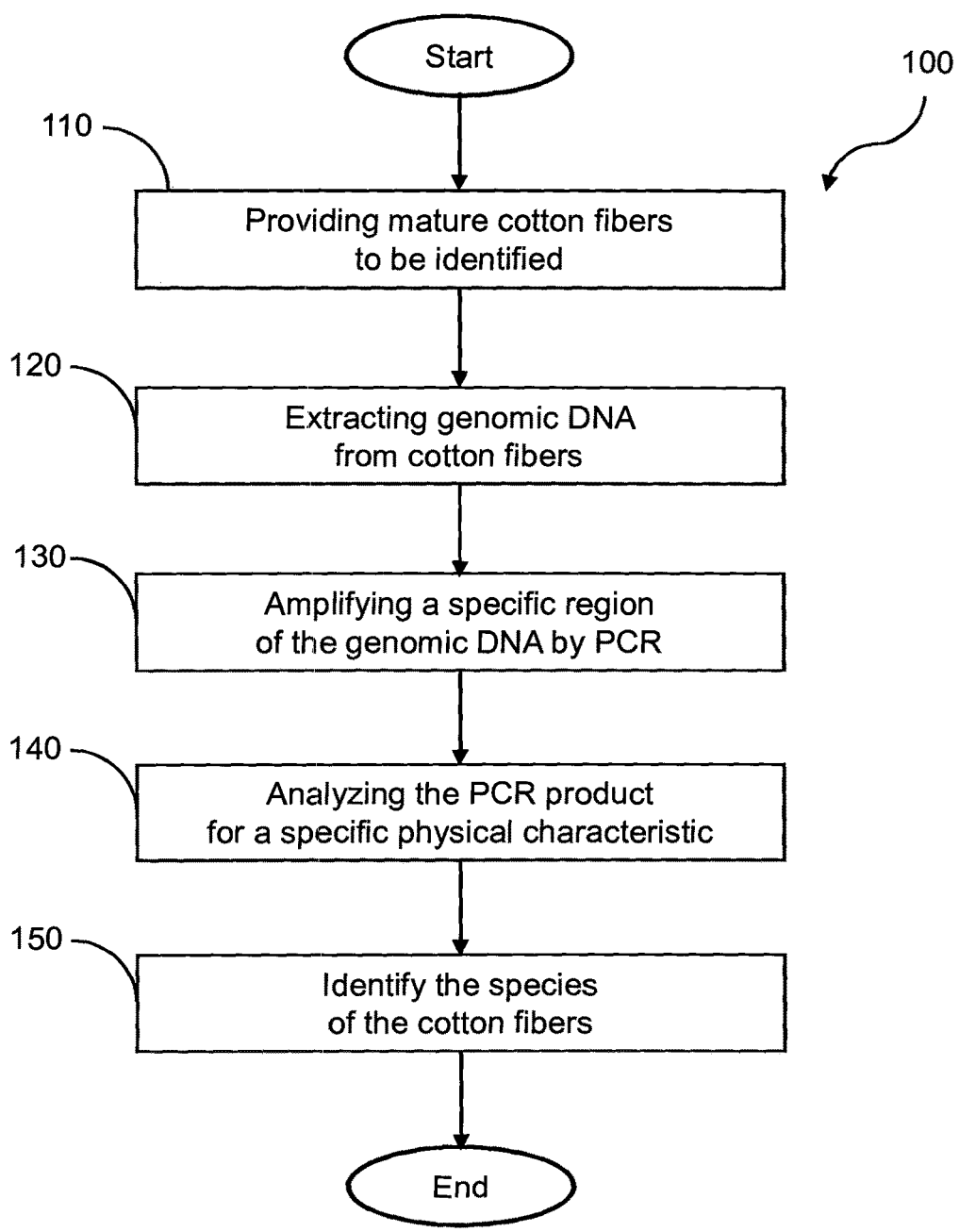
FIG. 2 is a flow chart of one embodiment of the methods for identifying the cotton species of mature cotton fibers.

FIG. 2 is a flow chart illustrating one embodiment of a method 100 for identifying the species of mature cotton fibers. At event 110, mature cotton fibers are collected and/or obtained from a cotton source. The cotton source may be raw cotton fibers from a specific geographical location, from a cotton textile, cotton article or garment, or from a source where the species is already known. The cotton fibers may also be from anthropological textiles as well as fibers from artwork canvases or any other article where knowing the cotton species utilized for an article would be advantageous in verifying or authenticating the item. The method and kit allows for verification of articles in a manner that helps prevent forgers and counterfeiters from substituting false or counterfeit goods in place of authentic items.

At event 120, the method 100 further comprises extracting genomic DNA from the collected cotton fibers. In general, a variety of nucleic acid extraction solutions have been developed over the years for extracting nucleic acid sequences from a sample of interest. See, for example, Sambrook et al. (Eds.) *Molecular Cloning*, Cold Spring Harbor Press, 1989. Many such methods typically require, for example, a detergent-mediated step, a proteinase treatment step, a phenol and/or chloroform extraction step, and/or an alcohol precipitation step. Some nucleic acid extraction solutions may comprise an ethylene glycol-type reagent or an ethylene glycol derivative to increase the efficiency of nucleic acid extraction while other methods only use grinding and/or boiling the sample in water. Other methods, including solvent-based systems and sonication, could also be utilized in conjunction with other extraction methods.

In most embodiments, about 5 mg to about 30 mg of cotton fiber or cotton lint, and in certain instances between about 10 mg to about 15 mg of cotton fibers are needed for sufficient DNA to be extracted from the sample for analysis. DNA extraction protocols are derived from standard molecular biology DNA extraction procedures, which can be easily accomplished by persons skilled in the art.

Analysis and Cloning of Eukaryotic Genomic DNA

1. Depending on the type of sample, carry out one of the following procedures as step 1.

Protocol I

Drop freshly excised tissue into liquid nitrogen in the stainless-steel cup of a Waring Blendor. Blend at top speed until the tissue is ground to a powder. Allow the liquid nitrogen to evaporate, and add the powdered tissue little by little to approximately 10 volumes of extraction buffer (10 mM Tris.Cl (pH 8.0), 0.1 mM EDTA (pH 8.0), 20 µg/ml pancreatic RNAase, 0.5% SDS) in a beaker. Allow the powder to spread over the surface of the extraction buffer, and then shake the beaker to submerge the material. When all of the material is in solution, transfer the solution to a 50-ml centrifuge tube, incubate for 1 hour at 37° C., and then proceed to step 2.

2. Add proteinase K to a final concentration of 100 µg/ml. Using a glass gently mix the enzyme into the viscous solution. Proteinase K is stored as a stock solution at a concentration of 20 mg/ml in $H_2O$.

3. Place the suspension of lysed cells in a water bath for 3 hours at 50° C. Swirl the viscous solution periodically.

4. Cool the solution to room temperature, and, if necessary, pour the solution into a centrifuge tube. Add an equal volume of phenol equilibrated with 0.5 M Tris.Cl (pH 8.0) and gently mix the two phases by slowly turning the tube end over end for 10 minutes. If the two phases have not formed an emulsion at this stage, place the tube on a roller apparatus for 1 hour. Separate the two phases by centrifugation at 5000 g for 15 minutes at room temperature. It is essential that the pH of the phenol be approximately 8.0 to prevent DNA from becoming trapped at the interface between the organic and aqueous phases.

5. With a wide-bore pipette (0.3 cm-diameter orifice), transfer the viscous aqueous phase to a clean centrifuge tube and repeat the extraction with phenol twice. When transferring the aqueous phase, it is essential to draw the DNA into the pipette very slowly to avoid disturbing the material at the interface. If the DNA solution is so viscous that it cannot easily be drawn into a wide-bore pipette, use a long pipette attached to a water-suction vacuum pump to remove the organic phase. Make sure that the phenol is collected into traps and does not enter the water line. With the vacuum line closed, slowly lower the pipette to the bottom of the organic phase. Wait until the viscous thread of aqueous material detaches from the pipette, and then carefully open the vacuum line and gently withdraw all of the organic phase. Close the vacuum line and quickly withdraw the pipette through the aqueous phase. Immediately open the vacuum line to transfer the residual phenol into the trap. Centrifuge the DNA solution at 5000 g for 20 minutes at room temperature. Protein and clots of DNA sediment to the bottom of the tube. Pour the DNA solution into a 50-ml centrifuge tube, leaving behind the protein and clots of DNA.

6. To isolate very-high-molecular-weight DNA (~200 kb): After the third extraction with phenol, dialyze the pooled aqueous phases at 4° C. four times against 4 liters of a solution of 50 mM Tris.Cl (pH 8.0) 10 mM EDTA (pH 8.0) until the $OD_{270}$ of the dialysate is less than 0.05. Allow room in the dialysis bag for the volume of the sample to increase 1.5 to 2.0-fold. Continue to step 7.

To isolate DNA whose size is 100-150 kb: After the third extraction with phenol, transfer the pooled aqueous phases to a fresh centrifuge tube and add 0.2 volume of 10 M ammonium acetate. Add 2 volumes of ethanol at room temperature and swirl the tube until the solution is thoroughly mixed. The DNA will immediately form a precipitate that can usually be removed from the ethanolic solution with a pasteur pipette whose end has been sealed and shaped into a U. Most of the contaminating oligo-nucleotides are left behind. If the DNA precipitate becomes fragmented collect it by centrifugation at 5000 g for 5 minutes at room temperature in a swinging-bucket rotor. Wash the DNA precipitate twice with 70% ethanol, and collect the DNA by centrifugation as described above. Remove as much as possible of the 70% ethanol, and store the pellet in an open tube at room temperature until the last visible traces of ethanol have evaporated. Do not allow the pellet of DNA to dry completely; otherwise, it will be very difficult to dissolve. Add 1 ml of TE (pH 8.0) for each ~$5 \times 10^6$ cells. Place the tube on a rocking platform and gently rock the solution until the DNA has completely dissolved. This usually takes 12-24 hours.

7. Measure the absorbance of the DNA at 260 nm and 280 nm. The ratio of $A_{260}$ to $A_{280}$ should be greater than 1.75. A lower ratio is an indication that significant amounts of protein remain in the preparation. In this case, add SDS to a concentration of 0.5% and then repeat steps 2-7.

8. Calculate the concentration of the DNA (a solution with an $OD_{260}$ of 1 contains approximately 50 µg of DNA per milliliter), and analyze an aliquot by pulsed-field gel electrophoresis or by electrophoresis through a 0.3% agarose gel poured on a 1% agarose support. The DNA should be larger than 100 kb in size and should migrate more slowly than linear dimeric molecules of intact bacteriophage λ DNA. Store the DNA at 4° C.

Protocol II

This method, which is adapted from Bowtell (1987), is used to prepare DNA simultaneously from many different samples of cells or tissues.

1. Prepare cell suspensions (or frozen cell powders) as described in step 1 of protocol I.

2. Transfer the cell suspensions to centrifuge tubes, and add 7.5 volumes of lysis solution consisting of 6 M guanidine HCl ($M_r$=95.6), 0.1 M sodium acetate (pH 5.5).

If the DNA is to be extracted from tissues, add the frozen cell powders to approximately 7.5 volumes of lysis solution in beakers. Allow the powders to spread over the surface of the lysis solution, and then shake the beakers to submerge the material. When all the material is in solution, transfer the solution to centrifuge tubes.

3. Close the tops of the tubes and incubate for 1 hour at room temperature on a rocking platform.

4. Dispense 18 ml of ethanol at room temperature into each of a series of disposable 50-ml poly-propylene centrifuge tubes. Using wide-bore pipettes, carefully layer the cell suspensions under the ethanol.

5. Recover the DNA from each tube by slowly stirring the interface between the cell lysate and the ethanol with a pasteur pipette whose end has been sealed and bent into a U shape. The DNA will adhere to the Pasteur pipette, forming a gelatinous mass. Continue stirring until the ethanol and the aqueous phase are thoroughly mixed.

6. Transfer each pasteur pipette, with its attached DNA, to a separate polypropylene tube containing 5 ml of ethanol at room temperature. Leave the DNA submerged in the ethanol until all of the samples have been processed.

7. Remove each pipette, with its attached DNA, and allow as much ethanol as possible to drain away. By this stage, the DNA should have shrunk into a tightly packed, dehydrated mass, and it is often possible to remove most of the free ethanol by capillary action by touching the U-shaped end of the pipette to a stack of Kimwipes. Before all of the ethanol has evaporated from the DNA, transfer the pipette into a fresh polypropylene tube containing 5 ml of ethanol at room temperature.

8. When all of the samples have been processed, remove each pipette with its attached DNA, and remove as much ethanol as possible as described in step 7 above. Do not allow the pellet of DNA to dry completely-otherwise, it will be very difficult to dissolve.

9. Transfer each pipette to a fresh polypropylene tube containing 1 ml of TE (pH 8.0). Allow the DNAs to rehydrate by storing the tubes overnight at 4° C.

10. By the next morning, the DNAs will have become highly gelatinous but will still be attached to their pipettes. Using fresh, sealed pasteur pipettes as scrapers, gently free the pellets of DNA from their pipettes. Discard the pipettes, leaving the DNAs floating in the TE. Close the tops of the tubes and incubate the DNAs at 4° C. on a rocking platform until they are completely dissolved. This often takes 24-48 hours.

11. Analyze an aliquot by pulsed-field gel electrophoresis or by electrophoresis through a 0.3% agarose gel poured on a 1% agarose support. The DNA should be ~80 kb in size and should migrate more slowly than monomers. Store the DNA at 4° C.

Notes i. DNA made by this procedure is always contaminated with a small amount of RNA. It is therefore necessary to estimate the concentration of DNA in the final preparation either by fluorimetry or by gel electrophoresis and staining with ethidium bromide. If desired, the amount of contaminating RNA can be minimized by transferring the rehydrated pellet of DNA (step 10) to a fresh polypropylene tube containing 1 ml of TE (pH 8.0) before scraping it from the pasteur pipette. This is a hazardous procedure, since there is a risk that the DNA will slide off the pipette during transfer.

Partial Digestion of Eukaryotic DNA with Restriction Enzymes

The only method by which DNA can be fragmented in truly random fashion irrespective of its base composition and sequence, is mechanical shearing. However, DNA prepared in this way requires several additional enzymatic manipulations (repair of termini, methylation, ligation to linkers, digestion of linkers) to generate cohesive termini compatible with those of the vectors used to generate genomic DNA libraries (Maniatis et al. 1978). One hand, partial digestion with restriction enzymes that recognize frequently occurring tetranucleotide sequences within eukaryotic DNA yields a population of fragments that is close to random and yet can be cloned directly.

Fragments of eukaryotic DNA suitable for the construction of genomic DNA libraries are prepared as follows: Carry out pilot experiments to establish conditions for partial digestion of eukaryotic DNA. Guided by the results of the pilot experiments, digest a large amount of eukaryotic DNA and purify fragments of the desired size by density gradient centrifugation.

Pilot Experiments

1. Dilute 30 µg of high-molecular-weight eukaryotic DNA (>200 kb; see Protocol I) to 900 µl with 10 mM Tris.Cl (pH 8.0) and add 100 µl of the appropriate 10× restriction enzyme buffer.

If the concentration of the high-molecular-weight DNA is low, increase the volume of the pilot reactions and concentrate the DNA after digestion by precipitation with ethanol. Each pilot reaction should contain at least 1 µg of DNA to allow the heterogeneous products of digestion to be detected by staining with ethidium bromide. Handle the eukaryotic DNA carefully by using either pipette tips that have been cut off with a sterile razor blade to enlarge the orifice or disposable wide-bore glass capillaries. Make sure that the DNA is dispersed homogeneously throughout the buffer used for digestion. The chief problem encountered during digestion of high-molecular-weight DNA is unevenness of digestion caused by variations in the local concentration of DNA. Clumps of DNA are relatively inaccessible to restriction enzymes and can be digested only from the outside. Unless the DNA is evenly dispersed, the rate of digestion cannot be predicted or controlled. To ensure homogeneous dispersion of the DNA:

a. Allow the DNA to stand at 4° C. for several hours after dilution and addition of 10× restriction enzyme buffer.

b. Gently stir the DNA solution from time to time using a sealed glass capillary.

c. After addition of the restriction enzyme, gently stir the solution for 2-3 minutes at 4° C. before warming the reaction to the appropriate temperature.

d. After digestion for 15-30 minutes, add a second aliquot of restriction enzyme and stir the reaction as described above.

2. Carry out test digestions on aliquots of the batch of diluted DNA that will be used to prepare fragments for cloning. The amount of enzyme necessary will vary for each batch of enzyme and preparation of DNA.

a. Using a wide-bore glass capillary or a cut-off disposable plastic pipette tip, transfer 60 µl of the DNA solution to a microfuge tube (tube 1). Transfer 30 µl of the DNA solution to each of nine additional labeled microfuge tubes. Stand the tubes on ice.

b. Add 2 units of the appropriate restriction enzyme to the first tube. Use a sealed glass capillary to mix the restriction enzyme with the DNA. Do not allow the temperature of the reaction to rise above 4° C. Using a fresh pipette tip, transfer 30 µl of the reaction to the next tube in the series. Mix as before, and continue transferring the reaction to successive tubes. Do not add anything to the tenth tube (no enzyme control), but discard 30 µl from the ninth tube. Incubate the reactions for 1 hour at 37° C.

c. At the end of the digestion, heat the reactions to 70° C. for 15 minutes to inactivate the restriction enzyme. After cooling the reactions to room temperature, add the appropriate amount of gel-loading buffer (0.25% bromophenol blue, 0.25% xylene cyanol FF, 30% glycerol in water). Mix the solutions gently, using a sealed glass capillary. Use a cut-off, disposable plastic pipette tip or a disposable wide-bore glass capillary to transfer the solutions to the wells of a 0.3% agarose gel poured on a 1% agarose support. Compare the size of the digested eukaryotic DNA with that of oligomers of bacteriophage λ DNA and plasmids (see notes to step 1).

Large scale Preparation of Partially Digested DNA

1. After conditions have been established in pilot experiments (see above), digest 100 µg of high-molecular-weight DNA with the appropriate amount of restriction enzyme for the appropriate time. To ensure that the conditions for the large-scale digestion are as identical as possible to those used in the pilot experiment, we prefer to set up replicas of the successful pilot reaction rather than a single large-scale reaction. In addition, if sufficient eukaryotic DNA is available, we recommend using three different concentrations of restriction enzyme that straddle the optimal concentration determined in the pilot experiment. At the end of the digestion, analyze an aliquot of the DNA in each digestion by gel electro-phoresis to make sure that the digestion has worked according to prediction. Until the results are available, store the remainder of the sample at 0° C.

2. Gently extract the digested DNA twice with phenol: chloroform. Precipitate the DNA with 2 volumes of ethanol at 0° C. and redissolve it in 200 µl of TE (pH 8.0).

3. Prepare a 10-40% continuous sucrose density gradient in a Beckman SW40 polyallomer tube (or its equivalent). The sucrose solutions are made in a buffer containing 10 mM Tris.Cl (pH 8.0), 10 mM NaCl, 1 mM EDTA (pH 8.0). Heat the DNA sample for 10 minutes at 68° C., cool it to 20° C., and load it onto the gradient. Centrifuge at 22,000 rpm for 22 hours at 20° C. in a Beckman SW40 rotor (or its equivalent).

4. Using a 19-gauge needle, puncture the bottom of the tube and collect 350-µl fractions.

5. Mix 10 µl of every other fraction with 10 µl of water and 5 µl of gel-loading buffer I (0.25% bromophenol blue, 0.25% xylene cyanol FF, 40% (w/v) sucrose in water). Analyze the size of the DNA in each fraction by electrophoresis through a 0.5% agarose gel, using oligomers of plasmid DNA as markers. Be sure to adjust the sucrose and salt concentrations of the markers to correspond to those of the samples.

6. Following electrophoresis, pool the gradient fractions containing DNA fragments of the desired size. Dialyze the pooled fractions against 2 liters of TE (pH 8.0) at 4° C. for 12-16 hours, with a change of buffer after 4-6 hours. Leave space in the dialysis bag for the sample to expand two-to threefold. Alternatively, if the volume of the pooled sample is sufficiently small, the DNA can be precipitated with ethanol without prior dialysis after first diluting the sample with TE (pH 8.0) so that the concentration of sucrose is reduced to below 10%.

7. Extract the dialyzed DNA several times with an equal volume of 2-butanol until the volume is reduced to about 1 ml. Add 10 M ammonium acetate to a final concentration of 2 M and precipitate the DNA with 2 volumes of ethanol at room temperature.

8. Dissolve the DNA in TE (pH 8.0) at a concentration of 300-500 µg/ml. Analyze an aliquot of the DNA (0.5 µg) by electrophoresis through a 0.5% agarose gel to check that the size distribution of the digestion products is correct.

Large Scale Preparation of Partially Digested DNA

1. After conditions have been established in pilot experiments (see above), digest 100 pg of high-molecular-weight DNA with the appropriate amount of restriction enzyme for the appropriate time. To ensure that the conditions for the large-scale digestion are as identical as possible to those used in the pilot experiment, we prefer to set up replicas of the successful pilot reaction rather than a single large-scale reaction. In addition, if sufficient eukaryotic DNA is available, we recommend using three different concentrations of restriction enzyme that straddle the optimal concentration determined in the pilot experiment. At the end of the digestion, analyze an aliquot of the DNA in each digestion by gel electrophoresis to make sure that the digestion has worked according to prediction. Until the results are available, store the remainder of the sample at 0° C.

2. Gently extract the digested DNA twice with phenol xhloroform. Precipitate the DNA with 2 volumes of ethanol at 0° C. and redissolve it in 200 µl of TE (pH 8.0).

3. Prepare a 10-40% continuous sucrose density gradient in a Beckman SW40 polyallomer tube (or its equivalent). The sucrose solutions are made in a buffer containing 10 mM Tris.Cl (pH 8.0), 10 mM NaCl, 1 mM EDTA (pH 8.0). Heat the DNA sample for 10 minutes at 68° C., cool it to 20° C., and load it onto the gradient. Centrifuge at 22,000 rpm for 22 hours at 20° C. in a Beckman SW40 rotor (or its equivalent).

4. Using a 19-gauge needle, puncture the bottom of the tube and collect 350-pl fractions.

5. Mix 10 µl of every other fraction with 10 µl of water and 5 µl of gel-loading buffer I (0.25% bromophenol blue, 0.25% xylene cyanol FF, 40% (w/v) sucrose in water). Analyze the size of the DNA in each fraction by electrophoresis through a 0.5% agarose gel, using oligomers of plasmid DNA as markers. Be sure to adjust the sucrose and salt concentrations of the markers to correspond to those of the samples.

6. Following electrophoresis, pool the gradient fractions containing DNA fragments of the desired size (e.g., 35-45 kb for construction of libraries in cosmids; 20-25 kb for construction of libraries in bacteriophage λ vectors such as EMBL3 and 4). Dialyze the pooled fractions against 2 liters of TE (pH 8.0) at 4° C. for 12-16 hours, with a change of buffer after 4-6 hours. Leave space in the dialysis bag for the sample to expand two to threefold. Alternatively, if the volume of the pooled sample is sufficiently small, the DNA can be precipitated with ethanol without prior dialysis after first diluting the sample with TE (pH 8.0) so that the concentration of sucrose is reduced to below 10%.

While extracting DNA from seeds and leaves from various cotton species is quite common for cotton genomics research, utilizing DNA from the mature cotton fibers is quite unusual and unique. The amount of DNA, as well as the integrity of the DNA isolated from mature cotton fibers, may not be adequate for researching genetic variability and relationships among a plurality of genotypes or cotton species. The use of cotton fibers as a DNA source in the present invention is, surprisingly, sufficient for identifying and distinguishing between at least two different cotton species. This is partly due to the simplicity of the genetic test performed in the methods of the invention, when compared to the plurality of genetic techniques needed to carry out polymorphism studies on a large number of various genotypes or a large number of cotton species.

The embodiment of FIG. 2, in event 130, further comprises amplifying a target sequence or specific DNA region of the cotton DNA genome extracted from the cotton fibers in event 120. Polymerase Chain Reaction procedures enable the target sequence within the cotton species genome to be amplified or copied to a detectable quantity. In general, amplification comprises temperature cycling of the genomic DNA sample in the presence of free nucleotides, a specific set of primers for the target DNA, and a polymerase, which allows the target DNA to be copied, i.e. amplified.

In Vitro Amplification of DNA by Polymerase Chain Reaction

Amplification Reactions

1. In a sterile 0.5-ml microfuge tube, mix in the following order:

sterile $H_2O$ 30 µl
10× amplification buffer 10 µl
mixture of four dNTPs, each at a concentration of 1.25 mM 16 µl
primer 1 (in 5 µl of $H_2O$) 100 pmoles
primer 2 (in 5 µl of $H_2O$) 100 pmoles
template DNA (up to 2 µg, depending on the concentration of target sequences)
$H_2O$ to a final volume of 100 µl 10× Amplification buffer:
   500 mM KCl
   100 mM Tris.Cl (pH 8.3 at room temperature)
   15 mM $MgCl_2$
   0.1% gelatin The pH of the mixture of dNTPs should be 7.0 (dNTPs are used at saturating concentrations (200 µM for each dNTP).

A stock solution of dNTPs (50 mM) should be adjusted to pH 7.0 with 1.0 NaOH to ensure that the pH of the final reaction does not fall below 7.1. Prepared solutions of dNTPs sold by commercial manufacturers are generally not adjusted to pH 7.0. For amplification of single sequences from mammalian genomic DNA, use 0.2-2 µg of DNA. The reaction mixture will then contain approximately 0.03-0.3 pg of a target sequence 500 bp in length. For amplification of target DNA cloned in a plasmid vector (e.g., for DNA sequencing), add 20 ng of linearized plasmid DNA. Because the optimal concentration of $Mg^{++}$ in the reaction is quite low, DNAs to be used as templates should be dissolved in 10 mM Tris.Cl (pH 7.6), 0.1 mM EDTA (pH 8.0).

2. Heat the reaction mixture for 5 minutes at 94° C. to denature the DNA completely.

3. While the mixture is still at 94° C., add 0.5 µl of Taq DNA polymerase (5 units/µl; Perkin Elmer Cetus N801-0046).

Taq DNA polymerase is supplied in a storage buffer containing 50% glycerol. This solution is very viscous and is difficult to pipette with accuracy. The best method is to centrifuge the tube containing the enzyme at 12,000 g for 10 seconds at 4° C. in a microfuge and then to withdraw the required amount of enzyme using a positive-displacement pipetting device. Automatic pipetting devices are not recommended for handling reagents used in polymerase chain reactions.

4. Overlay the reaction mixture with 100 µl of light mineral oil (Sigma M-3516 or equivalent). This prevents evaporation of the sample during repeated cycles of heating and cooling.

5. Carry out amplification as described below. Typical conditions for denaturation, annealing, and polymerization are as follows:

| Cycle | Denaturation | Annealing | Polymerization |
|---|---|---|---|
| First cycle | 5 minutes at 94° C. | 2 minutes at 50° C. | 3 minutes at 72° C. |
| Subsequent cycles | 1 minute at 94° C. | 2 minutes at 50° C. | 3 minutes at 72° C. |
| Last cycle | 1 minute at 94° C. | 2 minutes at 50° C. | 10 minutes at 72° C. |

The denaturation step is omitted after the last cycle of amplification and the samples are transferred to −20° C. for storage.

Timing of individual steps should begin only after the reaction mixtures have reached the required temperatures. Between 30-60 seconds are required for reaction mixtures to reach the desired temperature after a temperature shift. The length of the lag depends on several factors, including the type of tube used, the volume of the reaction mixture, the source of the heat (water bath or heating block), and the temperature differential between successive steps. It is important to adjust the length of the incubation steps to compensate for these lags.

The temperature (50° C.) chosen for annealing of the oligonucleotide primers to the target DNA is a compromise. Amplification is more efficient if annealing is carried out at lower temperatures (37° C.), but the amount of mispriming is significantly increased (Saiki et al. 1988b). At higher temperatures (55° C.), the specificity of the amplification reaction is increased, but its overall efficiency is reduced. Ideally, a series of control reactions should be set up to determine the annealing temperature that gives optimal results for a given amplification reaction.

By comparing DNA genomic sequences of the two cotton species of interest, i.e. *G. barbadense* (GenBank Accession No. NC_008641) and *G. hirsutum* (GenBank Accession No. NC_007944), variable regions between the two species were detected and possible genetic markers to distinguish between these two cotton species were identified in these variable sequence regions. Utilizing primer software known to those skilled in the art, primers were identified and designed for the selected variable region(s) of the two cotton DNA sequences, allowing for the amplified PCR product to be identified as being from either *G. barbadense* or *G. hirsutum*. PCR primers were designed according to known criteria and PCR procedures may be conducted in commercially available instruments. Primers were designed to distinguish between the targeted sequences of the two species by exploiting the differences in at least one physical characteristic related to the targeted sequences. The "physical characteristic" utilized to distinguish between the two cotton species being either a detectable difference in length/size of the targeted sequence or a detectable DNA sequence variation (i.e. base substitution) specific for each of cotton species being analyzed.

Generally the primers designed for PCR amplification in event 130 utilize simple sequence repeats (SSR) or microsatellites which are polymorphic loci present in nuclear and organellar DNA (e.g. chloroplast DNA). Identifying regions comprising SSR's enables one set of primers to amplify a target sequence in either *G. barbadense* or *G. hirsutum*, with the target sequences from one species to the other being different in length due to the presence of varying number of SSR's found in the target sequence.

In some embodiments, nested set primers were utilized to achieve appropriate amplification of the targeted variable region of the two cotton species. Again, these nested set primers were identified and designed utilizing primer software and the genomic sequences of the cotton species of interest using primer design methods known to those skilled in the art of primer design.

Examples of primers utilized in some of the embodiments of the methods are given below. The primer sequences given below are only exemplary and are not meant to be limiting in the scope for distinguishing or verifying cotton fibers as being either the *G. barbadense* or *G. hirsutum* cotton species.

Exemplary primers were designed for an intergenic region, or space, between the petN and psbM genes of genomic DNA. Utilizing a sequence insertion of approximately 51 bases found in the *G. hirsutum* species which is lacking in the *G. barbadense* species. Primer 1 (Seq. ID. No. 1) and Primer 2 (Seq. ID. No. 2) were designed to target as a sequence of 411 base pairs in length versus a 360 base pair sequence for the *G. hirsutum* species and the *G. barbadense* species, respectively. The sequences of this set of primers are the following:

```
Primer 1
                                      (Seq. ID. No. 1)
GTTGGGGAGAAACTGATCCA Primer 2
                                      (Seq. ID. No. 2)
AAAAAGGATTCAAATCTCACGTC
```

While the above example utilizes a variable region within an intron, it is also possible to utilize a variable region found within an exon or gene region. The targeted marker or sequence is also not limited to a variable region found in chloroplast DNA, but may also be located in nuclear genomic DNA, as well as mitochondrial DNA.

The method 100 illustrated in FIG. 2 further comprises analyzing the PCR product(s) for a specific physical characteristic related to only one of the cotton species of interest in event 140. When the identifying physical characteristic is the length or size of the PCR product produced in event 130, techniques which allow for efficient size differentiation between the PCR products produced by one cotton species over another are utilized. Gel electrophoresis, both agarose and polyacrylamide gels, depending on the size range of the PCR product(s) produced, are capable of distinguishing the varying sizes of the PCR product produced by either DNA from mature cotton fibers of *G. barbadense* or *G. hirsutum*. For example, when utilizing primers 1 and 2 for PCR amplification, a 1.5% agarose gel, stained with DNA binding dye ethidium bromide is sufficient to resolve the size differences of the PCR products produced by *G. barbadense* or *G. hirsutum*. Running standard size marker controls on a gel with the PCR products produced from the methods enables the length (e.g. number of base pairs) of the PCR product to be determined.

In other embodiments, where the physical characteristic of the PCR products being analyzed in event 140 is size/length, a capillary electrophoresis device such as an AB1310 genetic analyzer can be utilized to determine the size of the PCR product(s) produced. For capillary electrophoresis, the length of the DNA amplicon produced by PCR is determined by extrapolating size data from an internal control run with the sample of known size. In general, the size resolution of the capillary electrophoresis is capable of distinguishing between amplicons which differ by only about 1 base pair. The sensitivity of capillary electrophoresis enables in some embodiments the use of primers which target variable regions of the cotton species where the difference between the size of the *G. barbadense* amplicons and the *G. hirsutum* amplicons is less than about 10 base pairs but greater than about 1 base pair, and in some embodiments the size difference can be less than about 6 base pairs but greater than about 3 base pairs. Example 2 below shows the results of utilizing a target sequence which varies only by 6 base pairs between the two species.

In event 150, the species of the analyzed cotton fibers is determined. This determination can be made by comparing the identified length of the PCR products to the theoretical and actual known size of the targeted and amplified sequence for *G. barbadense* or *G. hirsutum*. The PCR products from known *G. barbadense* or *G. hirsutum* DNA may also be run on a gel during electrophoresis to aid in identifying the species from which the sample originated. Once the PCR product length as been determined by either gel electrophoresis, capillary electrophoresis or other similar DNA sizing techniques, the analyzed sample can be identified and confirmed as a particular cotton species.

In other embodiments, the physical characteristic being analyzed is not length but a partial DNA sequence specific to a particular species. In this situation, PCR amplification may be performed in the presence of a non-primer detectable probe which specifically binds the PCR amplification product produced by one species and not the other. PCR primers are designed according to known criteria and PCR may be conducted in commercially available instruments. The probe is preferably a DNA oligonucleotide specifically designed to bind to the amplified PCR product. The probe preferably has a 5' reporter dye and a downstream 3' quencher dye covalently bonded to the probe which allows fluorescent resonance energy transfer. Suitable fluorescent reporter dyes include 6-carboxy-fluorescein (FAM), tetrachloro-6-carboxy-fluorescein (TET), 2,7-dimethoxy-4,5-dichloro-6-carboxy-fluorescein (JOE) and hexachloro-6-carboxy-fluorescein (HEX). A suitable quencher dye is (4-(dimethy(amino)-phenyl)-azo)-benzoic acid (Dabcyl). These dyes are commercially available from Perkin-Elmer, Philadelphia, Pa. Detection of the PCR amplification product may occur at each PCR amplification cycle. At any given cycle during the PCR amplification, the amount of PCR product is proportional to the initial number of template copies. The number of template copies is detectable by fluorescence of the reporter dye. When the probe is intact, the reporter dye is in proximity to the quencher dye which suppresses the reporter fluorescence. During PCR, the DNA polymerase cleaves the probe in the 5'-3' direction separating the reporter dye from the quencher dye increasing the fluorescence of the reporter dye which is no longer in proximity to the quencher dye. The increase in fluorescence is measured and is directly proportional to the amplification during PCR. This detection system is now commercially available as the TaqMan® PCR system from Perkin-Elmer, which allows real time PCR detection.

A probe specific for the *G. barbadense* PCR product may be analyzed in the same or a separate PCR sample tube as the probe specific for the *G. hirsutum* PCR product. Utilizing real-time PCR, the signal from a probe corresponding to a specific cotton species will identify which cotton species has been collected.

Figure 3:
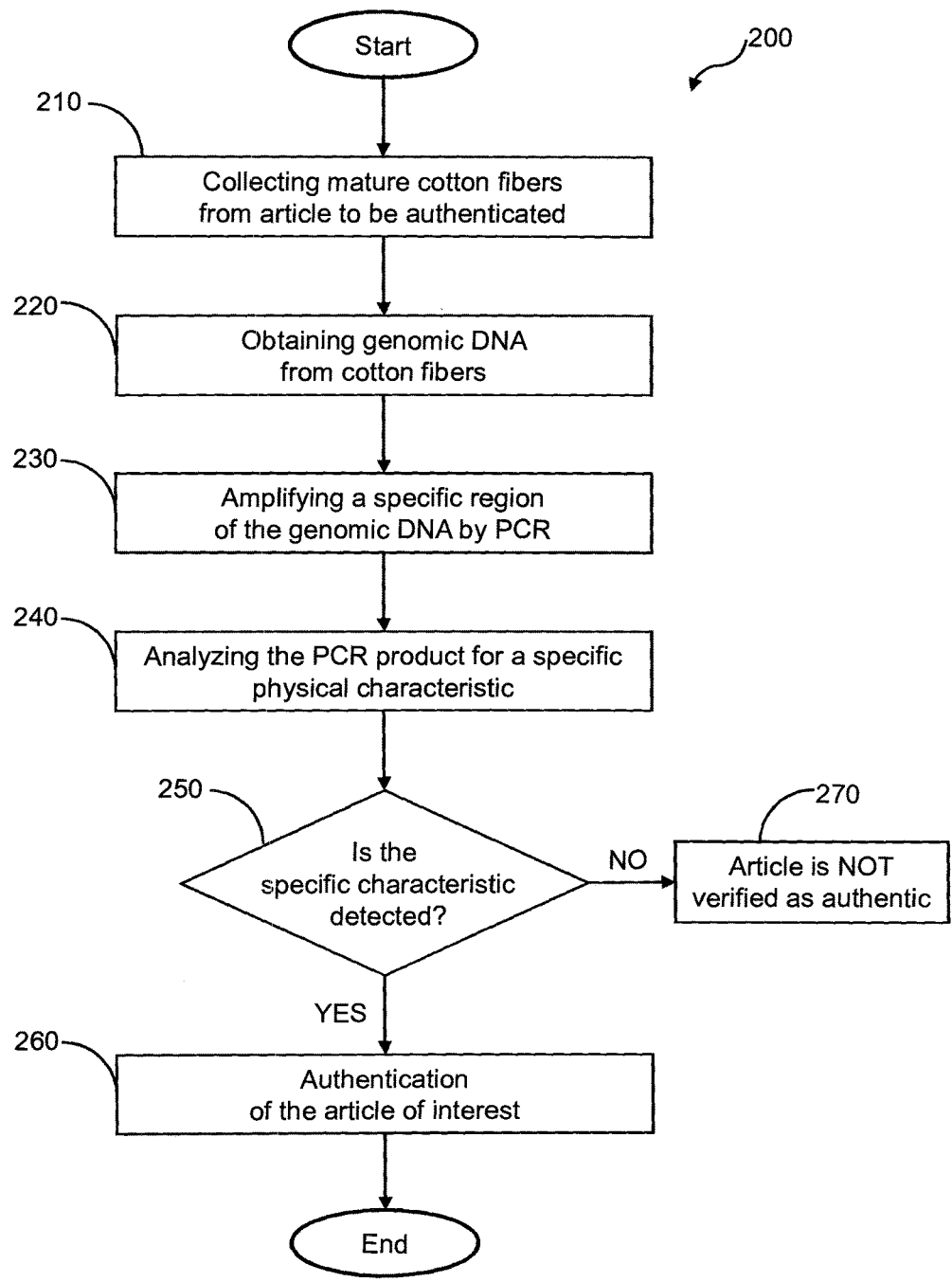
FIG. 3 is a flow chart of one embodiment of the methods for authenticating an article.

FIG. 3 is a flow chart illustrating generally a method 200 for authenticating or identifying an article as being manufactured with a specified cotton species. Usually verifying or authenticating an article occurs after the article has been introduced into a supply chain. Frequently, counterfeiters and forgers have the best access to articles after they are being shipped from the manufacturer/producer to wholesale or retail outlets or locations. With the methods described herein, a producer can track and authenticate articles or goods, allowing for better monitoring of when and where counterfeit goods are being replaced with forgeries or otherwise altered. When the article has entered a supply chain, a manufacturer or an authorized individual can collect a sample from the article at any desired point along the supply chain for authentication purposes. On other occasions, manufacturers deliberately replace higher quality raw materials (cotton fibers) with lower quality ones, in order to lower costs. However, by doing this, manufacturers not only violate labeling laws and licensing agreements, but also damage consumer confidence regarding brand name products.

The method 200 comprises, at event 210, collecting mature cotton fibers from an article to be authenticated. Collecting a sample may involve scraping, cutting or dissolving a portion of the article to obtain a cotton fiber sample for analysis. The collecting of the sample may be carried out, for example, by cutting the article to remove mature cotton fibers from the article. The sample collecting in other embodiments may be achieved by tweezing, scraping, or abrading the article with appropriate sampling tools configured to remove a sufficient amount of cotton fibers or cotton lint for analysis. Collecting fiber samples may, for example, occur at any point along the supply or commerce chain where there is concern about or risk of introduction of counterfeit articles.

The method 200 for authenticating an article further comprises, in event 220, obtaining or extracting genomic DNA from the collected cotton fibers. Extraction, isolation or purification of the genomic DNA obtained in the sample may be required. A variety of nucleic acid extraction solutions have been developed over the years for extracting nucleic acid sequences from a sample of interest. See, for example, Sambrook et al. (Eds.) "Molecular Cloning", (1989) Cold Spring Harbor Press. Many such methods typically require one or more steps of, for example, a detergent-mediated step, a proteinase treatment step, a phenol and/or chloroform extraction step, and/or an alcohol precipitation step. Some nucleic acid extraction solutions may comprise an ethylene glycol-type reagent or an ethylene glycol derivative to increase the efficiency of nucleic acid extraction, while other methods use only grinding and/or boiling the sample in water. Other methods, including solvent-based systems and sonication, could also be utilized in conjunction with other extraction methods.

The authentication method 200 further comprises, in event 230, amplifying a specific region of the extracted genomic DNA by PCR based techniques. The procedures and techniques for PCR amplification of a targeted sequence are similar to those described above in the methods illustrated in FIG. 2. There are numerous cultivars of both *G. barbadense* and *G. hirsutum*, which are utilized in the manufacturing of cotton textiles worldwide. The primers designed and selected in many embodiments enable a user to distinguish between the two species, *G. barbadense* or *G. hirsutum* independent of the type of cultivar or strain of the species. In other embodiments primers, may be selected and used for distinguishing other cotton species, such as *G. arboreum* and *G. herbaceum*.

The method 200 for authenticating an article further comprises, in event 240, analyzing the PCR product for a specific physical characteristic, such as length of the PCR product or a specific DNA sequence associated with a specific cotton species (e.g. *G. barbadense* or *G. hirsutum*). Analyzing the PCR product produced is generally the same as described above in the methods illustrated in FIG. 2. Numerous ELS cultivars have been shown to produce the identical or very similar length PCR products, which are easily identifiable as *G. barbadense* and are distinguishable from various Upland cultivars of *G. hirsutum*. Example 1 below describes the identification results of various cultivars in more detail. When the aim is to authenticate a cotton textile as either being *G. barbadense* or *G. hirsutum* cotton, a simplistic analysis is preferred. In many instances, a textile shipment may be on a stringent time table and a quick but accurate test is required. Utilizing primers which recognize a difference in length of a target sequence between the two species fulfills the desire for a quick and reliable verification test.

In event 250, the results of the analysis of the collected sample are reviewed and a query or determination is made as to whether or not a physical characteristic (i.e. known PCR product length) for a particular species was detected in the sample. If the physical characteristic associated with a particular cotton species nucleic acid is not found or not detected in the collected sample of the textile article at event 250, the conclusion at event 270 from the analysis is that the article is not made from that particular cotton species and may have been tampered with or substituted. If the physical characteristic associated with the cotton species is detected in the sample at event 250, then the article is verified in event 260 as being authentic.

If a determination is made in event 270 that an article is not authentic, a different, earlier point in the supply or commerce chain may be selected and events 210 through 250 may be repeated. Thus an article from an earlier point in the supply chain would be selected, cotton fibers collected, and analyzed. If it is again determined that the article is not authentic or has been otherwise tampered with, then events 210-250 may be repeated with an article selected from yet an earlier point in the supply chain. In this manner, the time and/or location of tampering or counterfeit substitution of the textile article may be located.

Kits for verifying cotton fibers and authenticating articles of interest incorporate the methods described herein. The kits may comprise, for example, a container of the nucleic acid extraction buffer, and a sample tube for holding a collected mature cotton fiber sample of the item or article to be authenticated. The kits may further comprise at least one primer set configured to produce amplified PCR fragments from both ELS and Upland genomic DNA. The kits may include a collection tool for taking a sample of the labeled article for transfer to the sample tube. The kits may also further comprise a portable electrophoretic device (e.g. gel apparatus or capillary electrophoresis system) for analyzing PCR products. The kits may also include an internal control for fragment size comparison for capillary analysis.

By way of example and not limitation, the collection tool of the kit may comprise a blade or scissors for cutting a piece of the article, or the like. The sample tube of the kit may include a sealable vial or Eppendorf tube, and may contain solvent or solution for extraction of the nucleic acids (e.g. DNA) from the sample taken from the textile article.

The kit may comprise primers and/or probes as well as solutions appropriate for PCR analysis. The kit may further comprise a small PCR instrument for analysis of the extracted nucleic acids from the mature cotton fibers.

The capillary electrophoresis device of the kit may comprise an internal control for detecting the fragment size of the amplified PCR product(s).

The illustrative kits thus provide a convenient, portable system for practicing the methods of the invention.

Illustrative methods for authenticating textile articles utilizing mature cotton fibers are provided in the following Examples.

EXAMPLES

The following preparations and examples are given to enable those skilled in the art to more clearly understand and to practice the present methods. They should not be considered as limiting the scope of the invention, but merely as being illustrative and representative thereof.

Example I

Differentiation of ELS and Upland Cotton Fibers.

Mature cotton fibers of 25 known cultivars from various regions around the world were tested with cotton specific SSRs primers, among which 15 samples are ELS (*G. barbadense*) and 10 samples are Upland *G. hirsutum* cotton.

TABLE 1

List of known cotton cultivars.
Samples are raw mature cotton fibers.

| # | name | ELS/Upland |
|---|---|---|
| 1 | Cobalt | ELS |
| 2 | DP 340 | ELS |
| 3 | DP 353 | ELS |
| 4 | E-503 | ELS |
| 5 | OA 353 | ELS |
| 6 | OA 353 EXP | ELS |

TABLE 1-continued

List of known cotton cultivars.
Samples are raw mature cotton fibers.

| # | name | ELS/Upland |
|---|---|---|
| 7 | PHY 820 | ELS |
| 8 | PHY 830 | ELS |
| 9 | PI MIXED | ELS |
| 10 | PO3X 8161 | ELS |
| 11 | PHY 800 | ELS |
| 12 | SJV EXP PIMA | ELS |
| 13 | Egyptian Giza 70 | ELS |
| 14 | Egyptian Giza 86 | ELS |
| 15 | Egyptian Giza 88 | ELS |
| 16 | CPCSD ACALA Fiesta RR | Upland |
| 17 | CPCSD ACALA Sierra RR | Upland |
| 18 | CPCSD ACALA Riata RR | Upland |
| 19 | CPCSD ACALA Daytona RF | Upland |
| 20 | Phytogen PHY72 | Upland |
| 21 | Phytogen PHY725 RF | Upland |
| 22 | Delta&Pine DP555 BG/RR | Upland |
| 23 | Lint444 | Upland |
| 24 | Lint445 | Upland |
| 25 | Lint555 | Upland |

For DNA extraction, 10-15 mg of mature cotton fibers were weighed and put into 1.5 ml Eppendorf tubes. DNA extraction protocols are derived from standard molecular biology DNA extraction procedures, which can be easily accomplished by people skilled in the art. Sample tubes were then vortexed and centrifuged briefly to be used as PCR templates. For DNA amplification, a PCR master mix containing 10 ul of amplification buffer, 0.5 ul of 10 uM forward and reverse primers, 5 ul of water, and 4 ul of DNA extracts were put into 0.2 ml thin wall PCR tubes and run for 40 cycles for DNA amplification. PCR anneal temperature and duration times were adjusted according to individual primer sets, and anyone familiar in the art of PCR will be able to design their own scheme. The primer set was designed in such a way that ELS cotton DNA produced 360 bp amplicons and the Upland cotton sample(s) produced 411 bp amplicons. The primer set comprised of Primer 1 and Primer 2, Primer 1 (Seq. ID. No. 1) having the sequence of GTTGGGGAGAAACTGATCCA, and Primer 2 (Seq. ID. No. 2) having the sequence of AAAAAGGATTCAAATCT-CACGTC. These primers are only exemplary to demonstrate the instant invention.

Those with ordinary skill in the art of designing primer sets would be able to produce a plurality of different primer sets other than those described above, which can distinguish between the two types of cotton analyzed here, given the genomic sequences of G. barbadense (GenBank Accession No. NC_008641) and G. hirsutum (GenBank Accession No. NC_007944). These specific primers are merely exemplary.

Figure 4:
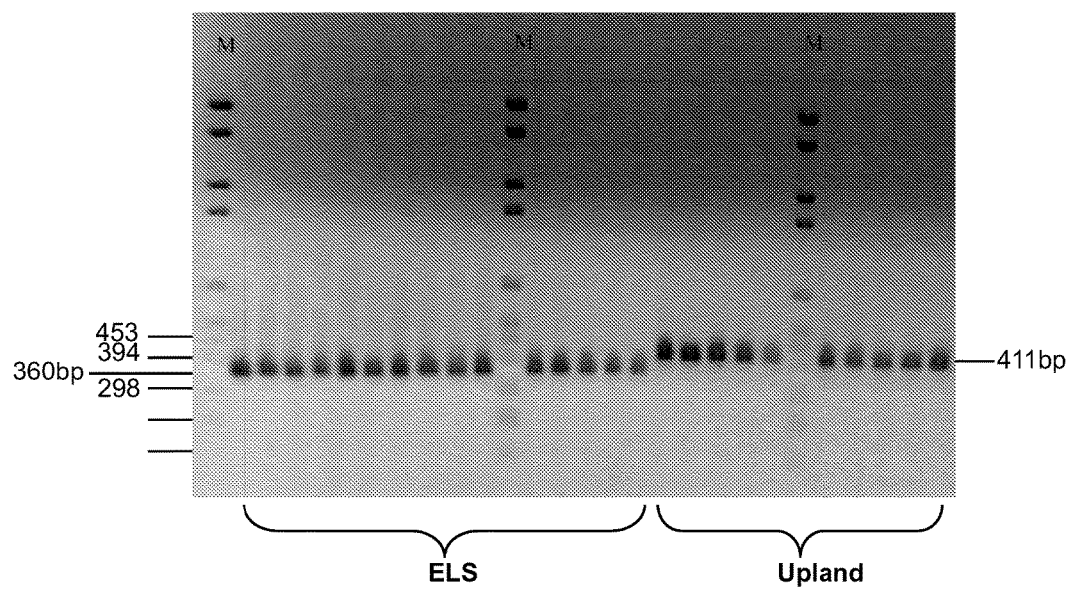
FIG. 4 is a photograph of an electrophoresis gel of DNA extracted from mature cotton fibers of known cultivars.

The PCR products were then analyzed by gel electrophoresis with a 1.5% agarose gel and stained with DNA binding dye ethidium bromide. Lengths of DNA fragments were calculated by extrapolating size data from standard molecular markers run on the same gel. FIG. 4 is a photograph of an agarose gel comprising electrophoretic results of the 25 samples described in Table 1. The gel electrophoresis photograph shows that G. barbadense samples #1-15 produced the same sized PCR DNA fragments (360 bp), while the PCR fragments produced by G. hirsutum samples #16-25 are of a larger size (411 bp). DNA fragment lengths were calculated by extrapolating size data from molecular marker run on the same gel.

This example demonstrates that ELS cotton fibers can be identified and authenticated as not being upland cotton fibers and visa versa, by standard gel electrophoresis techniques.

Example II

Differentiation of ELS and Upland Cotton Fabrics.

Fabrics made of either ELS or Upland cotton fibers were tested for genetic identification. For DNA extraction, 10-15 mg of fabrics were weighted and put into 1.5 ml Eppendorf tubes. DNA extraction protocols are derived from standard molecular biology DNA extraction procedures, which can be accomplished by those skilled in the art. Sample tubes were then vortexed and centrifuged briefly to be used as PCR templates. For DNA amplification, a PCR master mix containing 10 ul of amplification buffer, 0.5 ul of 10 uM forward and reverse primers, 5 ul of water, and 4 ul of DNA extracts were put into 0.2 ml thin wall PCR tubes and run for 40 cycles for DNA amplification. PCR annealing temperature and duration times were adjusted according to individual primer sets, and any one familiar in the art of PCR will be able to design their own scheme. The primer set was designed to take advantage of a 5 base pair deletion in a variable region between the psbZ-trnG intergenic space in the G. hirsutum genome versus the G. barbadense genome, in such way that ELS (G. barbadense) cotton DNA produced 237 bp amplicons and the Upland (G. hirsutum) produced 232 bp amplicons.

After PCR amplification, the PCR products were analyzed by capillary electrophoresis using an ABI310 genetic analyzer. DNA fragment sizes were calculated by extrapolating size data from utilizing an internal control included with the capillary electophoretic sample(s).

As the capillary electrophoresis electrogram shows, Sample #1's fragment is 237 bp in length, and Sample #1 is made of ELS cotton fibers; while Sample #2's fragment is 232 bp in length, and Sample #2 is made of Upland cotton fibers.

Figure 5:
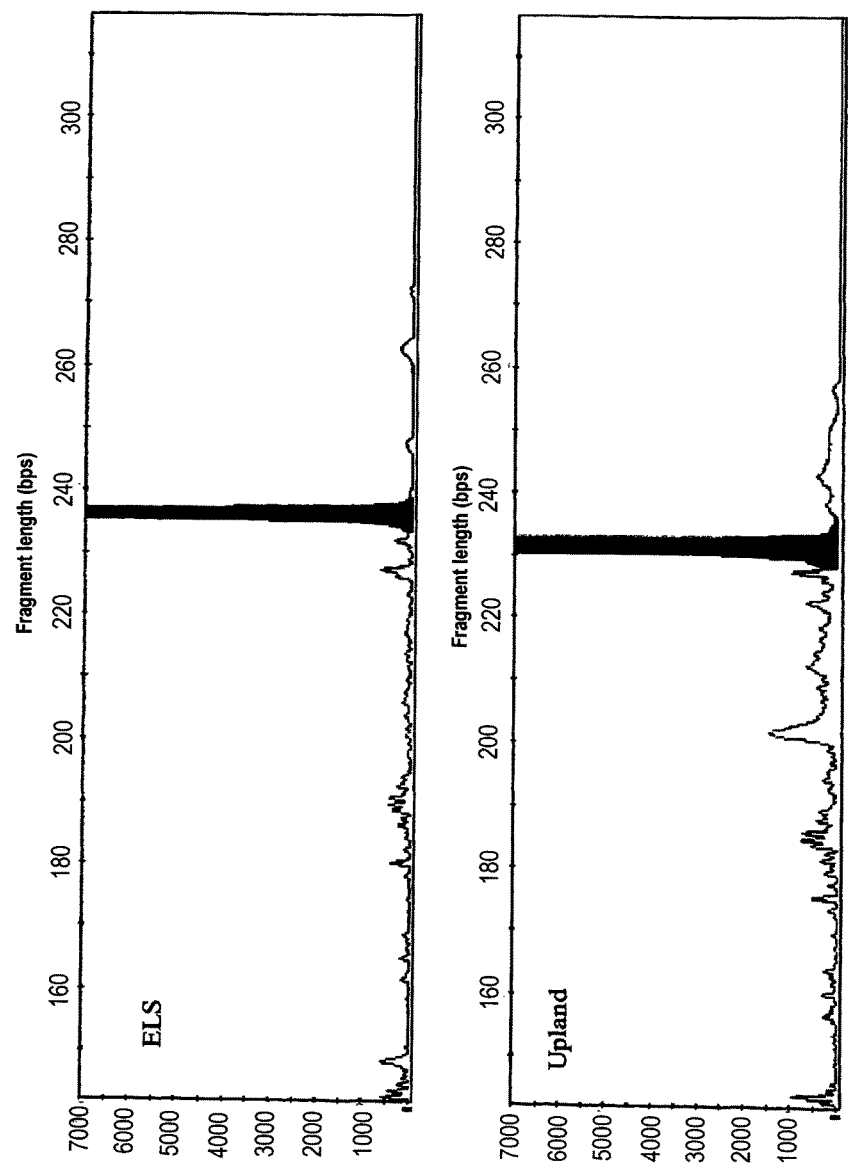
FIG. 5 is an electrogram of a capillary electrophoresis analysis of DNA extracted from cotton fabrics of known materials; Sample 1 is made of ELS cottons and Sample 2 is made of upland cottons.

FIG. 5 is an electrogram of a capillary electrophoresis analysis of PCR products produced from DNA extracted from cotton fibers collected from textile materials where the cotton species utilized to manufacture the item was known. Sample #1, fibers from a red cloth are identified and confirmed as ELS cotton; Sample #2, the T shirt cotton fibers, were determined to be from Upland cotton. The theoretical and detectable size for the amplified product from ELS cotton is 237 bp and the amplified product from upland cotton is 232 bp. This example demonstrates that cotton textile articles can be identified as made from ELS or Upland cotton species.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process step or steps, to the objective spirit and scope of the present invention. All such modifications are intended to be within the scope of the claims appended hereto.

What is claimed is:

1. A method for identifying mature cotton fibers from a manufactured article, the method comprising:
   providing one or more mature cotton fibers from the manufactured article;
   extracting chloroplast DNA from the mature cotton fibers;
   amplifying said chloroplast DNA with a PCR-based technique producing one or more amplified products;
   analyzing the one or more amplified products of the chloroplast DNA to distinguish between a first cotton species and a second cotton species by detecting a variation in a target sequence;
   identifying the one or more mature cotton fibers from the manufactured article as including a fiber from the first cotton species and/or a fiber from the second cotton species.

2. The method of claim 1 wherein the first cotton species is *G. barbadense*.

3. The method of claim 2 wherein the second cotton species is *G. hirsutum*.

4. The method of claim 3 wherein amplifying further comprises using at least one set of specific primers which target a sequence polymorphism between *G. barbadense* and *G. hirsutum*.

5. The method of claim 1 wherein the amplifying further comprises using at least one set of specific primers which target a sequence polymorphism between the first cotton species and the second cotton species.

6. The method of claim 1 further comprising analyzing the amplified products to distinguish between a first cotton species and a second cotton species based on different sequence length of the first cotton species compared with the second cotton species.

7. The method of claim 6 wherein the analyzing of the one or more amplified products further comprises detecting the length of the one or more amplified products by gel electrophoresis.

8. The method of claim 6 wherein the analyzing of the one or more amplified products further comprises detecting the length of the one or more amplified products by capillary electrophoresis.

9. The method of claim 1 wherein analyzing the amplified product to distinguish between a first cotton species and a second cotton species further comprises the use of a hybridizing probe specific for the target sequence of either the first or second cotton species.

10. The method of claim 1 wherein the manufactured article is a garment or a textile.

11. The method of claim 10 wherein the textile is selected from the group consisting of yarn, fabric, ginned cotton, an artwork canvas and an anthropological textile.

12. A method for identifying mature cotton fibers from a manufactured article, the method comprising:
    providing one or more mature cotton fibers from the manufactured article;
    extracting chloroplast DNA from the mature cotton fibers;
    amplifying said chloroplast DNA producing one or more amplified products;
    analyzing the one or more amplified products of the chloroplast DNA to distinguish between a first cotton species and a second cotton species by detecting a variation in a target sequence;
    identifying the one or more mature cotton fibers from the manufactured article as including a fiber from the first cotton species and/or a fiber from the second cotton species.

13. The method of claim 12 wherein the first cotton species is *G. barbadense*.

14. The method of claim 13 wherein the second cotton species is *G. hirsutum*.

15. The method of claim 12 wherein the amplifying further comprises using at least one set of specific primers which target a sequence polymorphism between the first cotton species and the second cotton species.

16. The method of claim 12 wherein the amplifying further comprises using at least one set of specific primers which target a sequence polymorphism between *G. barbadense* and *G. hirsutum*.

17. The method of claim 12, where the one of the first cotton species and the second cotton species is *G. arboreum*.

18. The method of claim 12, where the one of the first cotton species and the second cotton species is *G. herbaceum*.

19. The method of claim 12 wherein said manufactured article is obtained from a textile.

20. The method of claim 12 further comprising analyzing the amplified products to distinguish between a first cotton species and a second cotton species based on different sequence lengths of the first cotton species compared with the second cotton species.

21. The method of claim 12 wherein the manufactured article is a garment or a textile.

22. The method of claim 21 wherein the textile is selected from the group consisting of yarn, fabric, ginned cotton, an artwork canvas and an anthropological textile.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Sequence from Gossypium barbadense and
      Gossypium hirsutum cotton

<400> SEQUENCE: 1
gttggggaga aactgatcca                                              20

<210> SEQ ID NO 2
<211> LENGTH: 23
<212> TYPE: DNA
<213> ORGANISM: Artificial Sequence
<220> FEATURE:
<223> OTHER INFORMATION: Sequence from Gossypium barbadense and
      Gossypium hirsutum cotton

<400> SEQUENCE: 2
aaaaaggatt caaatctcac gtc                                          23